(12) United States Patent
Colvin et al.

(10) Patent No.: US 6,477,886 B1
(45) Date of Patent: Nov. 12, 2002

(54) APPARATUS FOR MEASURING THE AMOUNT OF AIR ENTRAINED IN A FLUID

(75) Inventors: Alex David Colvin, Oak Park, MI (US); Kenneth Miller Junkins, Ann Arbor, MI (US)

(73) Assignee: Ford Global Technologies, Inc., Dearborn, MI (US)

( * ) Notice: Subject to any disclaimer, the term of this patent is extended or adjusted under 35 U.S.C. 154(b) by 0 days.

(21) Appl. No.: 09/697,694

(22) Filed: Oct. 26, 2000

(51) Int. Cl.⁷ ............................. G01N 7/00; E21B 47/00
(52) U.S. Cl. .................................... 73/19.05; 73/152.04
(58) Field of Search ................... 73/19.01, 19.04, 73/19.05, 19.07, 19.1, 23.2, 152.04; 96/164, 200; 210/120, 604, 626

(56) References Cited

U.S. PATENT DOCUMENTS

| | | | | |
|---|---|---|---|---|
| 2,680,060 A | * | 6/1954 | Natelson | 422/88 |
| 3,521,478 A | * | 7/1970 | Magorien | 73/19.05 |
| 4,289,018 A | * | 9/1981 | Hellouin de Menibus | 73/19.04 |
| 4,887,464 A | * | 12/1989 | Tannenbaum et al. | 73/152.04 |
| 5,062,292 A | * | 11/1991 | Kanba et al. | 73/19.01 |
| 5,361,624 A | * | 11/1994 | Lambert et al. | 73/19.1 |
| 5,645,726 A | * | 7/1997 | Pollock | 210/626 |
| 5,664,416 A | * | 9/1997 | Sangret | 60/327 |
| 6,076,392 A | * | 6/2000 | Drzewiecki | 73/23.2 |

FOREIGN PATENT DOCUMENTS

JP        401203982    *   8/1989        G01R/31/12

OTHER PUBLICATIONS

Magorien, Keeping Air Out Of Hydraulic Systems, Aug. 7, 1980, Machine Design, pp. 71–76.*

* cited by examiner

Primary Examiner—Hezron Williams
Assistant Examiner—Jay L. Politzer
(74) Attorney, Agent, or Firm—Gregory P. Brown

(57) ABSTRACT

An apparatus (1) for measuring the amount of air entrained in the fluid of a power steering pump. The apparatus includes a fluid conduit (3) having a connector (4) adapted to connect to a power steering pump (2) with the fluid conduit (3) in fluid communication with the internal fluid cavity (5) of the power steering pump (2). A pressure gauge (6) is operatively connected to the fluid conduit (3) for determining the pressure in the power steering pump (2), and a meter (7) is operatively connected to the fluid conduit (3) for measuring the rate at which mass is removed from the power steering pump (2). The apparatus further includes a vacuum pump (8) operatively connected with the fluid conduit (3) for drawing air out of the power steering pump (2).

19 Claims, 2 Drawing Sheets

APPARATUS FOR MEASURING THE AMOUNT OF AIR ENTRAINED IN A FLUID

FIELD OF THE INVENTION

The present invention relates to a measurement apparatus, and in particular to an apparatus that is useful for measuring the volume of air entrained in the working fluid of a power steering pump.

BACKGROUND OF THE INVENTION

Automotive power steering systems typically include a hydraulic pump and control valve connected to the discharge side of the pump, which directs pressurized hydraulic fluid at a specific flow rate to the right or left-hand portions of the power steering gear depending upon the direction that the steering wheel of the vehicle is turned by the operator. Several kinds of hydraulic pumps are used in such systems including sliding vane, slipper or gerotor types. The pumps are usually belt driven from the engine shaft and adapted to produce a volumetric flow rate that varies in proportion to the speed of the engine.

During operation of the power steering pump, air and/or other gaseous substances may become entrained in the hydraulic fluid in the form of very small bubbles. The entrained air may result in excess noise during operation of the steering pump. The noises may include whining or hissing noises. Because these noises may be similar to these caused by improper functioning components, such noise may create difficulty in evaluating whether or not the power steering components are functioning properly.

Accordingly, it would be advantageous to be able to measure the amount of air entrained in the power steering fluid when diagnosing the source of excessive power steering pump noise.

SUMMARY OF THE INVENTION

One aspect of the present invention is to provide an apparatus for measuring the amount of air entrained in the fluid of a power steering pump. The apparatus includes a fluid conduit having a connector adapted to connect to a power steering pump with the fluid conduit in fluid communication with the internal fluid cavity of the power steering pump. A pressure gauge is operatively connected to the fluid conduit for determining the pressure in the power steering pump, and a mass flow meter is operatively connected to the fluid conduit for measuring the rate at which mass is removed from the power steering pump. The apparatus further includes a vacuum pump operatively connected with the fluid conduit for drawing air out of the power steering pump.

Another aspect of the present invention is an apparatus for measuring the volume of a gaseous substance disposed within a container. The apparatus includes a vacuum pump adapted to be operatively connected with the container to generate a vacuum within the container, and a pressure gauge adapted to be operatively connected with the container to measure the pressure within the container. The apparatus further includes a device adapted to measure the change of mass within the container upon application of a vacuum to the container by the vacuum pump.

Yet another aspect of the present invention is a method for determining the amount of a gaseous substance entrained in the liquid of a power steering pump. The method includes removing a volume of the gaseous substance from a power steering pump by applying a vacuum to the liquid disposed in the power steering pump. The mass of the gaseous substance removed from the power steering pump is determined, and the change of pressure within the power steering pump resulting from the vacuum is also determined.

These and other features, advantages, and objects of the present invention will be further understood and appreciated by those skilled in the art by reference to the following specification, claims, and appended drawings.

DETAILED DESCRIPTION OF THE PREFERRED EMBODIMENT

Figure 1:
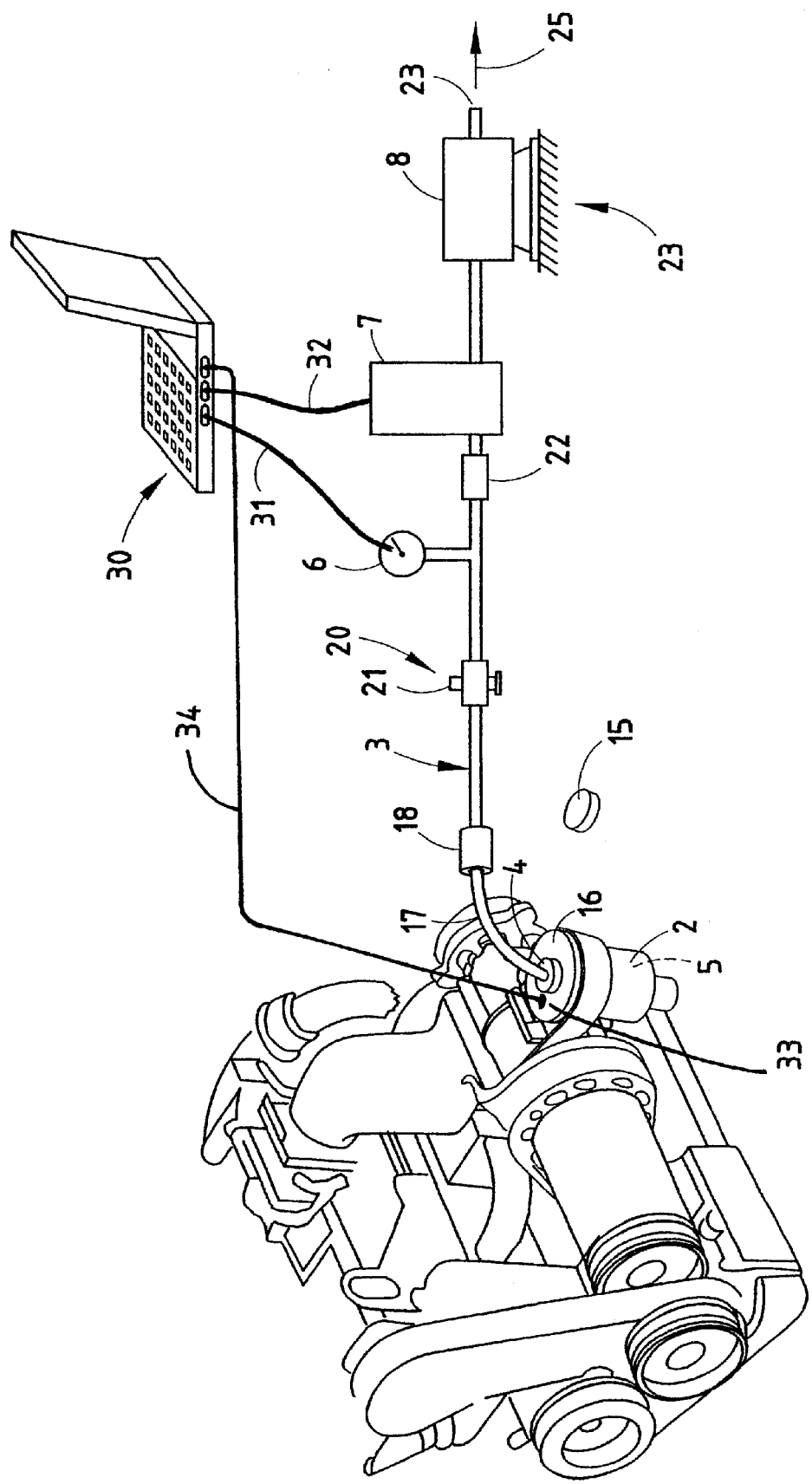
FIG. 1 is a fragmentary, partially schematic view of a measuring apparatus embodying the present invention connected to a power steering pump.

For purposes of description herein, the terms "upper," "lower," "right," "left," "rear," "front," "vertical," "horizontal," and derivatives thereof shall relate to the invention as oriented in FIG. 1. However, it is to be understood that the invention may assume various alternative orientations and step sequences, except where expressly specified to the contrary. It is also to be understood that the specific devices and processes illustrated in the attached drawings and described in the following specification are simply exemplary embodiments of the inventive concepts defined in the appended claims. Hence, specific dimensions and other physical characteristics relating to the embodiments disclosed herein are not to be considered as limiting, unless the claims expressly state otherwise.

The reference numeral 1 (FIG. 1) generally designates an apparatus for measuring the amount of a gaseous substance entrained in a fluid, which is particularly useful for measuring the amount of air entrained in the working fluid of a power steering pump 2. The apparatus includes a fluid conduit 3 having a connector 4 adapted to connect to the power steering pump 2 with the fluid conduit 3 in fluid communication with the internal fluid cavity 5 of the power steering pump 2. An absolute pressure gauge 6 is operatively connected to the fluid conduit 3 for determining the pressure in the power steering pump 2. A mass flow meter 7 is operatively connected in line with the fluid conduit 3 for measuring the rate at which mass is removed from the power steering pump 2, and a vacuum pump 8 is operatively connected with the fluid conduit 3 for drawing air out of the power steering pump 2. The apparatus includes a fluid conduit 3 having a connector 4 adapted to connect to the power steering pump 2 with the fluid conduit 3 in fluid communication with the internal fluid cavity 5 of the power steering pump 2. An absolute pressure gauge 6 is operatively connected to the fluid conduit 3 for determining the pressure in the power steering pump 2. A mass flow meter 7 is operatively connected in line with the fluid conduit 3 for measuring the rate at which mass is removed from the power steering pump 2, and a vacuum pump 8 operatively connected with the fluid conduit 3 for drawing air out of the power steering pump 2.

Figure 3:
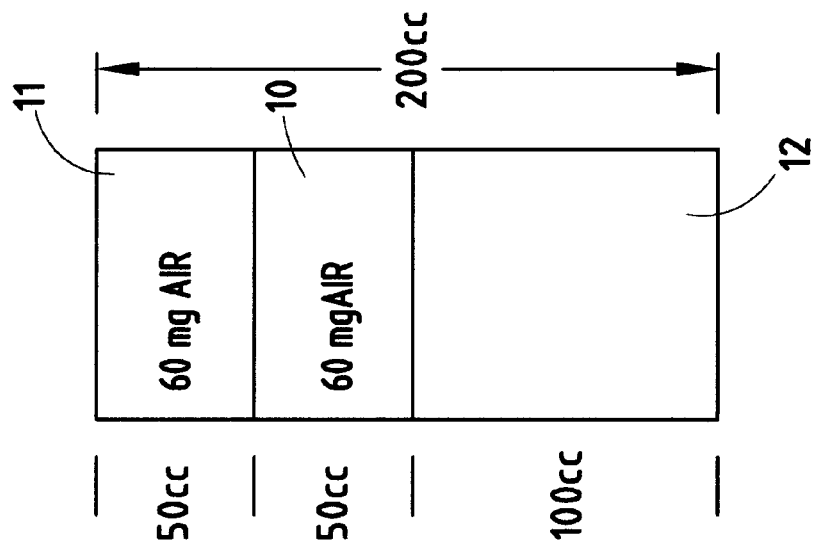
FIG. 3 is a graphical illustration of air within a container such as a power steering pump after application of a vacuum to remove entrained air.
Figure 2:
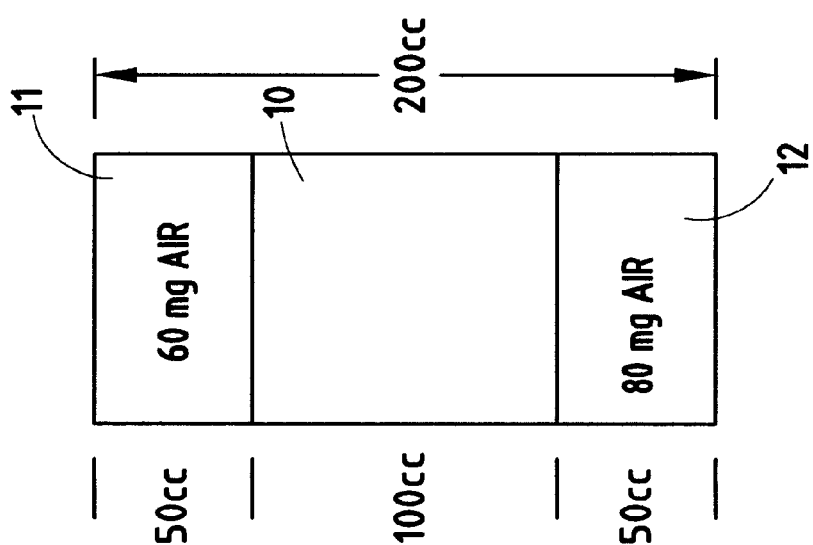
FIG. 2 is a graphical illustration of air within a container such as a power steering pump.

With further reference to FIG. 2, very small air bubbles become entrained, or mixed into, the working fluid of a power steering pump. These small air bubbles may contribute to the noise problems generated in the power steering pump. Although the size of such air bubbles entrained in the fluid varies, such bubbles are generally in the range of about 1–10 microns in diameter. The surface tension of the liquid acting on such small air bubbles compresses the air, such that the small bubbles have increased density relative to larger bubbles in the same liquid. For example, with reference to FIG. 2, at atmospheric pressure a 200 cubic centimeter (cc) container such as a power steering pump may include 100 cc of liquid 10, and 60 milligrams of air in the form of large bubbles or other trapped air taking up 50 cc of volume. If an additional 80 milligrams of air are entrained in the liquid, the 80 milligrams of entrained air 12 will also occupy about 50 cc due to the greater density of the entrained air. In contrast, if no entrained air 12 is present in the 100 cc of liquid 10, a total of 120 milligrams of air will fill the remaining 100 cc of volume. The entrained air (FIG. 2) may be removed from the liquid 10 by application of a vacuum. The entrained air in the form of very small "compressed" bubbles may then be replaced with large bubbles or air above the surface of the liquid 10 by removing the vacuum, with the result that the 200 cc volume will contain 20 milligrams less air total (FIG. 3). Therefore, if the total weight of the air or other gaseous substance and liquid is measured before and after removal of the entrained air 12, the amount of entrained air previously present in the liquid 10 can be determined.

With reference to FIG. 1, connector 4 comprises a threaded fitting that is connected to the threaded opening 16 of power steering pump 2 after removal of the power steering filler cap 15. The fluid conduit 3 comprises a rigid tubing having sufficient strength to prevent collapse upon actuation of the vacuum pump 8. In the illustrated example, the fluid conduit 3 comprises a 6.0 millimeters diameter rigid tubing able to withstand a vacuum of one-tenth atmosphere or less. An air trap 18 is disposed in the fluid conduit 3, and a first tubing section 17 of the fluid conduit 3 extends between the connector 4 and the trap 18. The trap 18 traps oil to prevent the oil from traveling to the pressure gauge 6, mass flow meter 7, and/or vacuum pump 8. Although the exact shape and size of the trap 18 is not critical, in the illustrated example, trap 18 comprises a cylindrical volume of about 100 cc.

A three-way valve 20 is positioned adjacent trap 18 in the fluid conduit 3, and includes an opening 21. Three way valve 20 can be turned to open the conduit 3 to the opening 21 of three-way valve 20, such that the internal cavity 5 of the power steering pump 2 is opened to ambient pressure. A capillary restriction 22 is positioned in the fluid conduit 3 between the pressure gauge 6 and the mass flow meter 7 to restrict the flow through the mass flow meter 7, thus ensuring that the mass flow remains within the capacity of the meter 7. Mass flow meter 7 is configured to measure the volume of air being removed, and is automatically corrected to standard temperature and pressure (STP). In the illustrated example, the capillary restriction has an inner diameter of approximately 0.020 inches, with a length of about 4 to 5 inches. The vacuum pump 8 is positioned at the end 23 of the fluid conduit 3, and exhausts air 25 through the exit 23 of the vacuum pump 8.

Pressure gauge 6 is operatively connected to a laptop or other computer 30 via an electrical line 31, and mass flow meter 7 is similarly operatively connected to the computer 30 by an electrical line 32. A temperature gauge 33 for measuring the temperature of the power steering fluid in power steering pump 2 is also operatively connected to the computer 30 via an electrical line 34.

To start the test, the filler cap 15 is first removed from the power steering pump 2, and the connector 4 is threadably connected to the power steering pump 2. The three-way valve 20 is then opened to permit the internal cavity 5 of the power steering pump 2 to reach ambient pressure. The computer 30 then stores the measurement of the mass flow meter 7 at the zero flow condition to establish a zero flow value of the signal from the mass flow meter 7. The absolute temperature from the temperature gauge at the start of the test is also measured and stored by the computer 30. The three-way valve is then turned to close opening 21 and permit flow through the three-way valve 20 to the vacuum pump 8.

The vacuum pump 8 is then actuated to begin evacuation of air from the power steering pump 2. The mass flow measured by the mass flow meter is taken at small time intervals, and the mass flow rate is numerically integrated over the time period to determine the total mass passing through the mass flow meter 7. During the test, the vacuum pump 8 will continue to evacuate air from the power steering pump 2 until a desired pressure, such as, for example, one-tenth atmosphere, within the power steering pump 2 is reached. Alternately, the test may be run for a selected time interval. At the end of the test, the final pressure and temperature are stored by the computer. The computer then calculates the volume of the air removed during the test according to the following equation:

Let V1=Air Volume in Power steering pump when open to the air because the liquid is incompressible, V1 also= Volume of air in power steering pump after evacuation while under vacuum.

V=Volume of air removed as measured with Mass Flow Meter (automatically corrected to STP). Then, $$V1 = V*At/TC0/(Pb/TC1 - Pf/TC2)$$

Where: V=integration of mass flow readings with time
At=standard atmospheric pressure (760 mm Hg)
TC0=standard absolute temperature (273 deg K)
Pb=absolute pressure before evacuation
Pf=absolute pressure at end of evacuation
TC1=absolute temperature before evacuation
TC2=absolute temperature at end of evacuation
V1=calculated volume of air in power steering pump Two basic equations are utilized to derive this equation. First, the mass of air that was originally in the volume being measured equals the mass of air removed from the volume plus the mass of air remaining in the volume. Second, the mass of air is proportional to the volume times the absolute pressure divided by the absolute temperature.

Thus, if the volume times the absolute pressure divided by the absolute temperature from the second equation is substituted into the first equation, and the proportionality constant is divided out, the following equation results:

$$V1*Pb/TC1 = V*At/TC0 + V1*Pf/TC2$$

Solving for V1:

$$V1 = V*At/TC0/(Pb/TC1 - Pf/TC2)$$

During this portion of the test, the entrained air bubbles will expand, and the entrained air will be drawn out of the liquid within the power steering pump 2.

The test cycle described above is then repeated a second time by turning off the vacuum pump 8, and opening three-way valve 20 to return the power steering pump 2 to the ambient pressure. Three-way valve 20 is then closed, and the initial pressure, temperature and mass flow meter readings are taken as described above. The vacuum pump 8 is then actuated, and the final pressure and temperature readings are taken. The volume of air removed from the power steering pump 2 is then calculated as described above. However, because the entrained air was substantially removed from the working fluid within the power steering pump 2 during the first test cycle, the second volume calculated will be less than the first volume calculated if such entrained air had been present. The difference between the first and second volumes of air removed from the power steering pump is then determined, and this difference in volumes is equal to the amount of air that was originally entrained in the fluid within the power steering pump 2. The volume of the entrained air can then be taken in a ratio relative to the total volume of fluid in the power steering system, and this ratio can then be utilized to determine if an acceptable concentration of entrained air is present in the power steering fluid. If the concentration of entrained air is sufficiently low, the user can readily determine that the source of the noise was not caused by entrained air, and further evaluation of the power steering system can be conducted to determine the source of the noise.

The apparatus of the present invention provides a system whereby a user can quickly and easily determine if entrained air is present in the power steering fluid to assist in determining the cause of noises generated by the power steering pump. The system is relatively compact and portable, thus facilitating field evaluation of such noises.

It will be understood by those who practice the invention and those skilled in the art, that various modifications and improvements may be made to the invention without departing from the spirit of the disclosed concept. The scope of protection afforded is to be determined by the claims and by the breadth of interpretation allowed by law.

The invention claimed is:

1. An apparatus for measuring the amount of air entrained in the fluid of a power steering pump, said apparatus comprising:
   a fluid conduit having a connector adapted to connect to a power steering pump with said fluid conduit in fluid communication with the internal fluid cavity of the power steering pump;
   a pressure gauge operatively connected to said fluid conduit for determining the pressure in the power steering pump;
   a temperature gauge adapted to be operatively connected to a power steering pump for measuring the temperature of liquid inside the power steering pump;
   a meter operatively connected to said fluid conduit for measuring the rate at which mass is removed from the power steering pump; and
   a vacuum pump operatively connected with said fluid conduit for drawing air out of the power steering pump.

2. The apparatus set forth in claim 1, wherein:
said fluid conduit includes a trap between said connector and said vacuum pump, said trap configured to trap larger bubbles to prevent travel of larger bubbles through said fluid conduit.

3. The apparatus set forth in claim 2, wherein:
said trap is formed by section of said fluid conduit having larger cross-sectional areas relative to adjacent portions of said fluid conduit.

4. The apparatus set forth in claim 3, wherein:
said trap has a volume of at least about one hundred cubic centimeters.

5. The apparatus set forth in claim 1, including:
a valve operatively connected to said fluid conduit and configured to selectively open said fluid conduit to ambient pressure.

6. The apparatus set forth in claim 5, wherein:
said valve is a three way valve configured to selectively close off at least a first portion of said conduit to prevent air flow to said vacuum pump, said valve simultaneously opening a second portion of said fluid conduit including said connector to ambient pressure to permit the internal fluid cavity of the power steering pump to reach ambient pressure.

7. The apparatus set forth in claim 6, wherein:
said fluid conduit includes a capillary restriction between said valve and said meter to restrict the flow of air to said meter from the power steering pump.

8. The apparatus set forth in claim 7, wherein:
said meter comprises a mass flow meter providing a signal corresponding to the rate at which mass flows through said fluid conduit.

9. The apparatus set forth in claim 8, including:
a computer operatively connected to said pressure and temperature gauges and to said mass flow meter, said computer programmed to calculate the volume of air entrained in the fluid based upon the total mass removed from the power steering pump and the change in pressure within the power steering pump.

10. An apparatus for measuring the volume of a gaseous substance disposed within a container, said apparatus comprising:
   a vacuum pump adapted to be operatively connected with the container to generate a vacuum within the container;
   a temperature gauge adapted to be operatively connected to a power steering pump for measuring the temperature of liquid inside the power steering pump;
   a pressure gauge adapted to be operatively connected with the container to measure the pressure within the container; and
   a device adapted to measure the change of mass within the container upon application of a vacuum to the container by said vacuum pump.

11. The apparatus set forth in claim 10, wherein:
said device comprises a mass flow meter; and including:
   a fluid conduit having a first end adapted to connect to the container, said vacuum pump connected with a second end of said fluid conduit, said pressure gauge and said meter connected to said fluid conduit between said first and second ends thereof.

12. The apparatus set forth in claim 11, including:
a three-way valve connected to said fluid conduit between said first end and said pressure gauge, said three way valve configured to selectively close off flow to said pressure gauge and simultaneously open said first end to ambient pressure.

13. The apparatus set forth in claim 12, wherein:
said pressure gauge is configured to provide a signal corresponding to the absolute pressure within said fluid conduit.

14. The apparatus set forth in claim 13, including:
a computer operatively connected to said pressure gauge and said mass flow meter, said computer programmed to calculate the volume of air entrained in the fluid based upon the total mass removed from the power steering pump and the change in pressure within the power steering pump.

15. A method for determining the amount of a gaseous substance entrained in the liquid of a power steering pump, said method comprising:

setting the pressure within the interior volume of a power steering pump to ambient pressure;

removing a first volume of the gaseous substance from the interior volume of the power steering pump by applying a vacuum to the liquid disposed in the power steering pump;

determining a first mass of the gaseous substance removed from the power steering pump;

returnig the interior volume to ambient pressure;

returning the interior volume of the power steering pump to ambient pressure;

removing a second volumne of gaseous substance from the interior volume of the power steering pump by applying a vacuum to the liquid disposed in the power steering pump;

determinig a second mass of the gaseous substance removed from the power steering pump;

determining the amount of gaseous substance entrained in the liquid by taking the difference between the first and second masses.

16. The method set forth in claim 15, including:

measuring the absolute change of pressure within the power steering pump; and calculating the volume of gaseous substance removed from the power steering pump based upon the change in absolute pressure within the power steering pump and the mass of the gaseous substance removed from the power steering pump.

17. The method set forth in claim 15, wherein:

a first instrument is used to measure the mass flow rate from the power steering pump;

a second instrument is used to measure the pressure within the power steering pump; and wherein:

a computer is operatively connected to the first and second instruments and calculates the volume of the gaseous substance entrained in the fluid of the power steering pump.

18. The method set forth in claim 17, wherein:

a fluid conduit is threadably connected to the power steering pump, and the first and second instruments are operably connected to the fluid conduit; and a three-way valve is connected to the fluid conduit and selectively closes off the fluid conduit and opens the power steering pump to ambient pressure.

19. The method set forth in claim 15, wherein:

the first and second volumes removed are measured; and the temperature of the liquid is measured and utilized to determine the first and second masses based upon the first and second volumes.

* * * * *